United States Patent [19]

Tenten et al.

[11] Patent Number: 5,677,261
[45] Date of Patent: Oct. 14, 1997

[54] PREPARATION OF A CATALYST CONSISTING OF A CARRIER AND A CATALYTICALLY ACTIVE OXIDE MATERIAL APPLIED TO THE SURFACE OF THE CARRIER

[75] Inventors: Andreas Tenten, Maikammer; Peter Weidlich, Mannheim; Gerd Linden, Heidelberg, all of Germany

[73] Assignee: BASF Aktiengesellschaft, Ludwigshafen, Germany

[21] Appl. No.: 562,595

[22] Filed: Nov. 24, 1995

[30] Foreign Application Priority Data

Nov. 29, 1994 [DE] Germany ............... 44 42 346.2

[51] Int. Cl.$^6$ .................................... B01J 21/04
[52] U.S. Cl. .................... 502/439; 502/523; 502/311; 502/312; 502/316; 502/321
[58] Field of Search ................... 502/523, 514, 502/321, 312, 311, 316, 439

[56] References Cited

U.S. PATENT DOCUMENTS 3,956,377  5/1976  Dolhyj et al. ............... 502/321
4,034,060  7/1977  Koberstein et al. .
4,560,673 12/1985  Shaw ....................... 502/206

FOREIGN PATENT DOCUMENTS 0 017 000  10/1980  European Pat. Off. .
WO 95/26820 10/1995  WIPO .

Primary Examiner—Steven Bos
Assistant Examiner—Thomas G. Dunn, Jr.
Attorney, Agent, or Firm—Oblon, Spivak, McClelland, Maier & Neustadt, P.C.

[57] ABSTRACT

A catalyst which consists of a carrier and a catalytically active oxide material applied to the surface of the carrier is prepared by a process in which the carrier is first moistened with, as an adhesive liquid, an aqueous solution of an organic substance boiling at above 100° C. at atmospheric pressure and a layer of active oxide material is then bonded to the surface of the moistened carrier by bringing it into contact with dry, finely divided active oxide material and the adhesive liquid is then removed from the moistened carrier coated with active oxide material.

19 Claims, No Drawings

PREPARATION OF A CATALYST CONSISTING OF A CARRIER AND A CATALYTICALLY ACTIVE OXIDE MATERIAL APPLIED TO THE SURFACE OF THE CARRIER

FIELD OF THE INVENTION

The present invention relates to a process for the preparation of a catalyst which consists of a carrier and a catalytically active oxide material applied to the surface of the carrier, in which the carrier is first moistened with an adhesive liquid (a liquid binder), a layer (coat) of active oxide material is then bound (applied) to the surface of the moistened carrier by bringing it into contact with dry, finely divided, active oxide material, and the adhesive liquid is then removed from the moistened carrier coated with active oxide material.

The present invention furthermore relates to catalysts which consist of a carrier and a catalytically active oxide material applied to the surface of the carrier and which are defined as coated catalysts, and to the use of such coated catalysts.

BACKGROUND OF THE INVENTION

It is generally known that oxidative chemical reactions can often advantageously be carried out in the gas phase over catalytically active oxides. Thus, DE-A 23 51 151 relates to the catalytic oxidation, ammoxidation and oxidative dehydrogenation of olefins of 3 to 5 carbon atoms over a catalytically active oxide material in the gas phase. Embodiments are, for example, the conversion of butadiene to maleic anhydride, of propene to acrolein, of acrolein to acrylic acid, of propene to acrylonitrile and of 2-butene to butadiene. DE-A 16 42 921 and DE-A 21 06 796 describe the catalytic gas phase oxidation of aromatic and unsatured hydrocarbons, naphthalene, o-xylene, benzene or n-butene to carboxylic acids or anhydrides thereof. Embodiments are, for example, the conversion of o-xylene to phthalic anhydride and of butadiene to maleic anhydride. DE-A 25 26 238 discloses that acrylic acid or methacrylic acid can be produced by catalytic gas-phase oxidation of acrolein or methacrolein over catalytically active oxide materials. DE-A 20 25 430 relates to the catalytic gas-phase oxidation of indanes to, for example, anthraquinone. In addition to oxygen, the catalytically active oxide material may contain only one other element or more than one other element (multielement oxide materials).

Catalytically active oxide materials which comprise more than one metallic element, in particular more than one transition metal, are particularly frequently used. In this case, the term multimetal oxide materials is used. Usually, multi-element oxide materials are not simple physical mixtures of oxides of the elemental constituents but heterogeneous mixtures of complex polycompounds of these elements.

As a rule, such catalytic gas-phase oxidations are carried out on a large industrial scale in fixed-bed reactors, ie. the reaction gas mixture flows through a fixed catalyst bed and the oxidative chemical reaction takes place during the residence time therein.

Most catalytic gas-phase oxidations are highly exothermic and are therefore advantageously carried out in practice in multiple contact tube fixed-bed reactors. The contact tube length is usually a few meters and the internal diameter of the contact tube is usually a few centimeters. Heat exchange media flowing around the contact tubes remove the process heat (cf. for example DE-A 44 31 957 and DE-A 44 31 949).

Fixed beds comprising finely divided, pulverulent, catalytically active oxide material are not very suitable for carrying out catalytic gas-phase oxidations since they are not usually capable of withstanding industrial loading with starting reaction gas mixture without hydraulic transport.

This means that the catalytically active oxide material is usually converted into moldings whose length is tailored to the internal diameter of the contact tube and is as a rule a few millimeters.

U.S. Pat. No. 4,366,093 generally recommends hollow cylinders (rings) as the preferred geometry of such moldings. The height and external diameter should be from 3 to 6 mm and the wall thickness from 1 to 1.5 mm. The only shaping methods considered by U.S. Pat. No. 4,366,093 are pelletizing or extrusion to give unsupported catalysts (the total hollow cylinder consists of catalytically active material which may be diluted with finely divided, inert material) or impregnation of carrier rings to give support catalysts. The disadvantage of annular unsupported catalysts having a wall thickness of $\leq 1.5$ mm is that the mechanical stability during introduction into the contact tube is not completely satisfactory. The disadvantage of supported catalysts is that they are limited to those oxidic active materials which can be formed from solutions. In addition, a single impregnation results only in slight absorption of active materials.

U.S. Pat. Nos. 4,438,217 and 4,522,671 recommend unsupported catalyst rings which have an external diameter of from 3 to 10 mm, an internal diameter which is from 0.1 to 0.7 times the external diameter and a height which is from 0.5 to 2 times the external diameter and are based on multimetal oxides containing molybdenum as the main component, for the preparation of acrolein or methacrolein by gas-phase catalytic oxidation. With a view to the required mechanical stability, 1 mm is considered to be just possible as a lower limit of the wall thickness. However, the disadvantage of larger wall thicknesses is that they are associated with an increase in the diffusion distance out of the reaction zone, which promotes undesirable secondary reactions and hence reduces the selectivity with respect to the desired product.

U.S. Pat. No. 4,537,874 likewise recommends catalyst beds comprising unsupported catalyst rings based on multimetal oxides containing molybdenum as the main component for the preparation of $\alpha,\beta$-monoethylenically unsaturated aldehydes by gas-phase catalytic oxidation. The wall thickness of the hollow cylinders is 2 mm in all examples.

Annular coated catalysts help to resolve the contradiction which exists in the case of unsupported catalyst rings between required mechanical stability (increasing wall thickness) on the one hand and limitation of the diffusion distance out of the reaction zone (decreasing wall thickness) on the other hand, while maintaining the otherwise particularly advantageous ring geometry. The mechanical stability is ensured by the annular carrier, and the catalytically active oxide material can be applied in the desired layer thickness to the ring surface.

However, a very general problem in the case of coated catalysts is their production on an industrial scale, ie. they are to be prepared on an industrial scale in such a way that

- they have the layer thickness required with regard to the catalyst activity,
- the catalytically active coat adheres satisfactorily in the required thickness to the surface of the carrier,
- the coat thickness shows very slight fluctuations over the surface of a carrier,
- the coat thickness shows very slight fluctuations over the surface of different carriers, the size of the specific, catalytically active surface area based on the mass unit of the active material is satisfactory and the output of the production process is satisfactory.

This applies in particular in the case of hollow cylindrical carriers whose rolling behavior, in contrast to carrier spheres, has a preferred direction and is responsible for the prior art processes for the preparation of coated catalysts having catalytically active oxide materials being essentially limited to spherical coated catalysts.

DE-A 20 25 430 discloses that coated catalysts based on catalytically active oxide materials can be prepared by applying the catalytically active material to the carrier by the plasma spray or flame spray method. The disadvantage with regard to the suitability of this method is that at least one main component must be fusible at the working temperature of the flame spray or plasma burner. Another disadvantage of this method is that the size of the specific catalytically active surface area is as a rule unsatisfactory. All embodiments of DE-A 20 25 430 are spherical coated catalysts. As a comparative example, DE-A 20 25 430 includes a process for the preparation of spherical coated catalysts, in which an aqueous solution containing oxalic acid and the catalytically active oxide material in dissolved form is sprayed onto hot carrier spheres. The disadvantage of this procedure is that it can be used only in the case of catalytically active oxide materials which are soluble in water. In addition, it leads to irregular coat thickness and unsatisfactory coat adhesion owing to the abrupt evaporation of the solvent at the surface of the hot carrier sphere. This procedure, too, results in not inconsiderable losses of active material.

DE-A 16 42 921 relates to the preparation of spherical oxidic coated catalysts by spraying a liquid containing the oxidic active material in dissolved or suspended form onto hot spherical carriers. DE-A 16 42 921 recommends water or an organic solvent, such as alcohol or formamide, as a solvent or suspending medium. Here too, the disadvantages include the fact that the water or solvent is evaporated virtually all at once as soon as the sprayed material comes into contact with the hot carrier, thus reducing the adhesive strength of the coat.

DE-A 25 10 994 corresponds essentially to DE-A 16 42 921, except that it includes annular carriers. It is also limited to catalytically active oxide materials which consist essentially of a vanadium/titanium mixed oxide.

DE-A 21 06 796 discloses the preparation of coated catalysts by spraying aqueous suspensions of the catalytically active oxidic material onto the agitated carriers. This procedure has the same disadvantages as described above for the spraying on of aqueous solutions containing the oxidic active materials in dissolved form. This applies in particular to spraying onto heated carriers. Even the recommended concomitant use of an aqueous polymer emulsion as a binder cannot remedy these disadvantages; rather, the presence of a polymer emulsion complicates the coating operation through film formation processes which are difficult to control. Although German Published Application DE-AS 21 06 796 also mentions cylinders as useful carriers, the embodiments do not include any corresponding examples.

DE-A 26 26 887 attempts to reduce the disadvantages of DE-A 21 06 796 by carrying out spraying of the aqueous suspension onto carrier spheres which are only at from 25° to 80° C. According to DE-A 29 09 671, page 5, column 10, this procedure may however result in the sprayed carrier elements sticking together. In order to increase the adhesive strength of the oxidic catalytically active coat to the surface of the carrier, DE-A 26 26 887 recommends the incorporation of inorganic hydroxy salts in the aqueous suspension to be sprayed on, which salts hydrolyze in aqueous solution to hydroxides and, after completion of the coated catalyst, form catalytically inert components of catalytically active oxide materials. However, the disadvantage of this measure is that it requires dilution of the oxidic active material. DE-A 26 26 887 also mentions rings and cylinders as possible carriers, but the examples as a whole are limited to spherical coated catalysts.

DE-A 29 09 670 corresponds essentially to DE-A 26 26 887. According to the description of DE-A 29 09 670, mixtures of water and alcohol may also be used as the suspending medium. After the suspension of the catalytically active oxide material has been sprayed on, the moisture content is eliminated by passing over hot air. The embodiments of DE-A 29 09 670 also include annular coated catalysts. However, only water is used as the suspending medium in all embodiments. The disadvantage of the procedure of DE-A 29 09 670 is the tendency of the sprayed moldings to agglomerate, as already mentioned with reference to DE-A 26 26 887. Furthermore, in the case of the annular coated catalysts, the resulting specific, catalytically active surface area of the coat of oxide material is generally unsatisfactory.

GB-1 331 423 relates to a process for the preparation of spherical oxidic coated catalysts, wherein an aqueous suspension or solution is formed from catalyst precursors and an organic assistant whose boiling point at atmospheric pressure is at least 150° C. and which is soluble in water, carriers are added to said suspension or solution and the liquid components are removed by evaporation with occasional stirring. The coated carriers thus obtained are then calcined and the catalyst precursor layer is converted into active oxide. The disadvantage of this procedure is that the resulting coated catalysts have relatively irregular coat thickness. Furthermore, the adhesion of the coat to the carrier surface is unsatisfactory since the calcination of the catalyst precursor material generally releases in an uncontrolled manner gaseous compounds which cause loosening of the structure.

EP-A 286 448 and EP-A 37 492 recommend the preparation of coated catalysts by the spray process described above or by the process of GB-1 331 423, with the disadvantages stated above.

EP-B 293 859 discloses a process for the preparation of spherical coated catalysts by using a centrifugal-flow coating apparatus. This procedure leads to particularly uniformly worked coat thicknesses, both over the individual sphere surface and over different sphere surfaces. However, the disadvantage of the procedure of EP-B 293 859 is that it recommends coating the carrier spheres not directly with the catalytically active oxide material but with a precursor material thereof. The latter is converted into the former by subsequent combustion (calcination) at elevated temperatures (a few hundred degrees Celsius). As a rule, the calcination is accompanied by spontaneous, ie. more or less uncontrolled, thermal decompositions of components present in the precursor material to give gaseous products which, on the one hand, result in the formation of special pore distributions and a large specific catalytically active surface area (up to 15 m$^2$/g) but on the other hand reduce the adhesion of the catalytically active coat to the surface of the carrier. Calcination after coating is also disadvantageous in that spoilt batches may be produced during calcination (for example in the case of an incorrect calcination atmosphere). Working up thereof is substantially more complicated when coating has already been carried out. EP-B 293 859 mentions water, alcohol and acetone as binders, in addition to ammonium nitrate, graphite and starch.

DE-A 23 51 151, U.S. Pat. No. 3,956,377 and DE-A 25 26 238 and disclose a process for the preparation of spherical oxide coated catalysts, in which the carrier spheres are first moistened with water or another liquid, such as petroleum ether, as a binder. The catalytically active oxide material is then applied to the binder-moistened carrier by rolling the moist carrier in the pulverulent catalytically active oxide material. The disadvantage of this procedure is that the achievable coat thickness is limited by the binder absorptivity of the carrier, since the binding of the total pulverulent oxide material to be taken up is dependent on this amount of binder taken up by the carrier. A further disadvantage of the method is that the degree of moistening of the particular surface layer during the coating process varies continuously, ie. the base layer comes into contact with the moisture of the uncoated carrier. The moisture then has to migrate initially through the base layer to the surface thereof in order to be able to bind further active material, etc. Consequently, an onion-like shell structure is obtained, the adhesion of successive layers to one another being particularly unsatisfactory. As a rule, the application of pressure causes the individual layers to peel away one after another. In all embodiments, the sole binder used is water.

DE-A 29 09 671 attempts to reduce the disadvantages of the procedure described there by introducing the spherical carriers into an inclined rotating turntable. The rotating turntable passes the spherical carriers periodically through two metering apparatuses arranged one after the other at a certain distance. The first of the two metering apparatuses corresponds to a nozzle through which the carrier spheres are sprayed with water and moistened in a controlled manner. The second metering apparatus is located outside the atomization cone of the water sprayed in and serves for feeding in the finely divided oxidic active material (for example via an oscillating conveyor). The carrier spheres moistened in a controlled manner take up the added catalyst powder, which is compacted to a cohesive coat on the outer surface of the carrier spheres as a result of the rolling movement. The carrier sphere provided in this manner with the base coat passes as, so to speak, fresh carrier once again through the spray nozzle in the course of the subsequent rotation, is moistened in the same controlled manner to enable it to take up a further layer of finely divided oxidic active material in the course of further movement, etc. The coat thickness can be adjusted essentially in a controlled manner by the method described. Furthermore, the homogeneity of the coat structure is improved. By passing in hot air, the water used as the binder can be finally removed. A further advantage of the procedured described is that the added finely divided oxidic active material can be such that it is completely taken up during the coating so that no losses of active material occur. However, a disadvantage of the procedure described is that the sole use of water as the binder does not produce completely satisfactory adhesion of the coat to the surface of the carrier sphere. In addition, the specific active surface of the resulting oxidic active material coat is in general not completely satisfactory.

SUMMARY OF THE INVENTION

It is an object of the present invention to provide a process for the preparation of a catalyst, consisting of a carrier and a catalytically active oxide material which is applied to the surface of the carrier, which process does not have the disadvantages of the prior art processes and is suitable in particular for the preparation of annular oxidic coated catalysts. The latter are particularly advantageous compared to spherical coated catalysts of identical active material, coat thickness and volume-specific activity in that they produce a smaller pressure drop along the fixed bed, ie. smaller partial pressures of the gaseous reactants build up at a given reactor loading (the amount of reaction mixture fed to the reactor per unit time). The result of this is that the hot spot which usually passes along the individual contact tube in the direction of flow during exothermic catalytic fixed-bed gas-phase oxidations has a reduced amplitude. This has an advantageous effect on the life of the oxidic active material used. A further advantage of annular coated catalysts over those having a spherical shape is that the temperature behavior of the tube-bundle reactor is less sensitive to fluctuations in the inlet temperature of the thermostating medium surrounding the contact tube. If, for example, this inlet temperature accidentally increases by one degree, the hot spot temperatures in the contact tubes usually increase by more than one degree. In annular coated catalysts (assuming identical active materials, coat thicknesses and volume-specific activity), however, this additional increase is smaller.

We have found that this object is achieved by a process for the preparation of a catalyst which consists of a carrier and a catalytically active oxide material applied to the surface of the carrier, in which the carrier is first moistened with a liquid binder, a layer of active oxide material is then bound to the surface of the moistened carrier by bringing it into contact with dry, finely divided, active oxide material, and the liquid binder is then removed from the moistened carrier coated with active oxide material, wherein the liquid binder used is a solution consisting of from 20 to 90% by weight of water and from 10 to 80% by weight of an organic compound whose boiling point or sublimation temperature at atmospheric pressure (1 atm) is >100° C., preferably >150° C. The organic content of the liquid binder to be used according to the invention is preferably from 10 to 50, particularly preferably from 20 to 30, % by weight.

DETAILED DESCRIPTION AND PREFERRED EMBODIMENTS OF THE INVENTION

Particularly suitable organic components of the novel liquid binder are monohydric and polyhydric organic alcohols, such as ethylene glycol, 1,4-butanediol, 1,6-hexanediol or glycerol, monobasic or polybasic organic carboxylic acids, such as propionic acid, oxalic acid, malonic acid, gluteric acid or maleic acid, amino alcohols, such as ethanolamine or diethanolamine, monofunctional or polyfunctional organic amides, such as formamide, and monosaccharides and oligosaccharides, such as glucose, fructose, sucrose or lactose. Preferred organic components are those whose boiling point or sublimation temperature at atmospheric pressure is below the calcination temperature used for producing catalytically active oxide material, or which decompose into gaseous components in the presence of oxygen on the catalytically active oxide material below this calcination temperature. The calcination temperature is usually $\leq 500°$ C., frequently $\leq 400°$ C. and in many cases $\leq 300°$ C. According to the invention, liquid binders whose boiling point at atmospheric pressure is above 100° C., preferably above 150° C., are particularly advantageous.

The advantageousness of the novel process in contrast to the use of pure water as the binder is believed to be due to, inter alia, the fact that the novel liquid binders are better capable of wetting both the finely divided oxidic active materials and the carriers.

The materials of the carriers are preferably chemically inert, ie. they do not essentially intervene in the course of the gas-phase oxidation which is catalyzed by the coated catalysts prepared according to the invention. According to the invention, particularly suitable materials for the carriers are alumina, silica, silates, such as clay, kaolin, steatite, pumice, aluminum silicate and magnesium silicate, silicon carbide, zirconium dioxide and thorium dioxide.

The surface of the carrier is advantageously rough since increased surface roughness generally results in greater adhesion of the applied coat to the oxidic active material. The surface roughness $R_z$ of the carrier is preferably from 40 to 200 µm, particularly preferably from 40 to 100 µm (determined according to DIN 4768 sheet 1 using a Hommel tester for DIN-ISO surface parameters from Hommelwerke). The carrier materials may be porous or nonporous. The carrier material is preferably nonporous (total volume of pores $\leq 1\%$ by volume, based on the volume of the carrier).

Any desired geometries of the carriers are in principle suitable for the novel process. Their longest dimension is as a rule from 1 to 10 mm. However, spheres or cylinders, in particular hollow cylinders, are preferably used as the carrier.

If cylinders are used as carriers, their length is preferably from 2 to 10 mm and their external diameter preferably from 4 to 10 mm. In the case of rings, the wall thickness is furthermore usually from 1 to 4 mm. Particularly preferred annular carriers have a length of from 3 to 6 mm, an external diameter from 4 to 8 mm and a wall thickness of from 1 to 2 mm. Rings having the geometry 7 mm×3 mm×4 mm (external diameter × length × internal diameter) are very particularly preferred.

The thickness of the catalytically active oxide material applied according to the invention to the carrier is advantageously as a rule from 10 to 1000 µm. Particularly in the case of annular carriers, from 10 to 500 µm are preferred, particularly preferably from 100 to 500 µm, very particularly preferably from 200 to 300 µm.

The fineness of the catalytically active oxide material to be applied to the surface of the carrier is of course adapted to the desired coat thickness. For the preferred range of a coat thickness from 100 to 500 µm, active material powders in which 50% of the powder particles pass through a sieve having a mesh size of from 1 to 10 µm and which contain less than 1% of particles having a longest dimension of more than 50 µm are particularly suitable. As a rule, the distribution of the longest dimensions of the powder particles corresponds to a Gaussian distribution as a result of the production.

In order to obtain the desired coat thickness, the novel process is advantageously repeated periodically, ie. the carrier provided with the base coat then forms the carrier first to be moistened and then to be coated by bringing it into contact with the dry, finely divided oxidic active material in the subsequent period according to the invention, etc.

In order to carry out the novel process on an industrial scale, it is therefore advisable to use the process principle disclosed in DE-A 29 09 671, but to use a novel liquid binder instead of water.

In this procedure, the carriers to be coated are introduced into a preferably inclined (the angle of inclination is as a rule from 30° to 90°) rotating container (for example a turntable or coating pan). The rotating container passes the carriers, which are in particular spherical or cylindrical, especially hollow cylindrical, through two metering apparatuses arranged a certain distance apart. The first of the two metering apparatuses advantageously corresponds to a nozzle through which the carriers rolling in the rotating turntable are sprayed with the liquid binder to be used according to the invention and are moistened in a controlled manner. The second metering apparatus is located outside the atomization cone of the liquid binder sprayed in and serves to feed in the finely divided oxidic active material (for example via an oscillating conveyor). The carrier spheres moistened in a controlled manner take up the supplied catalyst powder, which is compacted to a cohesive coat by the rolling movement on the outer surface of the cylindrical or spherical carriers (such compacting movement does not take place in the inner circle of a hollow cylindrical carrier and said circle therefore remains essentially uncoated).

If required, the carrier provided with a base coat in this manner once again travels past the spray nozzle in the course of the subsequent rotation is moistened in a controlled manner in order to be able to take up a further layer of finely divided oxidic active material in the course of further movement, etc. (intermediate drying is as a rule not necessary). The liquid binder used according to the invention can be removed, for example, by finally supplying heat, for example by the action of hot gases, such as $N_2$ or air. A particular advantage of the embodiment, described above, of the novel process is that coated catalysts having coats consisting of layers of two or more different active oxidic materials can be prepared in one operation. It is noteworthy that the novel process results in completely satisfactory adhesion both of the successive layers to one another and of the base layer to the surface of the carrier. This also applies in the case of annular carriers.

For the embodiment, described above, of the novel process, it is essential that moistening of the carrier surface to be coated is carried out in a controlled manner. In short, this means that the carrier surface is advantageously moistened in such a way that it contains adsorbed liquid binder but no liquid phase as such is observable on the carrier surface. If the carrier surface is too moist, the finely divided catalytically active oxide material agglomerates to give separate agglomerates instead of being adsorbed onto the surface. Details in this respect are given in DE-A 29 09 671.

An advantage of the novel process is that the final removal of the liquid binder used can be carried out in a controlled manner, for example by evaporation and/or sublimation. In the simplest case, this can be effected by the action of hot gases at an appropriate temperature (frequently from 50° to 150° C.). However, the action of hot gases can only effect preliminary drying. The final drying can then be carried out, for example, in a drying oven of any type (for example a belt dryer). The temperature used should not be above the calcination temperature employed for the preparation of the oxidic active material.

Surprisingly, it has been found that many of the polar organic binder components decompose on oxidic materials at elevated temperatures (which are below the abovementioned calcination temperature) and in the presence of atmospheric oxygen to give gaseous components, such as formic acid, $H_2O$, $CO_2$ or CO. Surprisingly, this is not as a rule accompanied by a reduction in the adhesion of the oxidic coat to the surface of the carrier. On the other hand, an increase in the specific surface area of the oxidic active material is achieved. This has made it possible for the first time to provide, for various oxidic active materials, annular coated catalysts which are completely satisfactory both with regard to the adhesive strength of the oxidic coat and with regard to the specific catalytic active surface area of the oxidic active material present in the coat.

In this publication, data with respect to the specific surface area A (m²/g) relate to determinations according to DIN 66131 (determination of the specific surface area of solids by gas adsorption ($N_2$) according to Brunauer-Emmet-Teller (BET)). Usually, they are carried out by first determining the surface area for the uncoated carrier and then that for the coated catalyst. The difference then gives the desired value for the oxidic active material of the coat. In many cases, the oxidic active material of the coat is diluted with finely divided, catalytically inert oxide (frequently oxides of Si, Al, Zr and/or Ti depending on the gas-phase reaction). Where the term specific surface area of the oxidic active material is used in this publication, this means the value of A excluding the contribution of this inert diluent. Since these inert diluents are generally added as such in the catalyst preparation, the contribution to both the surface area and the mass can be determined beforehand. A is obtained using the following relationship:

$$A = \frac{\text{Total surface area of the coat} - \text{surface area of the inert diluents contained in the coat}}{\text{Total mass of the coat} - \text{Mass of the inert diluents contained in the coat}}$$

Ie. A is the specific catalytic active surface area.

By suitable choice of liquid binder to be used according to the invention, it is possible, independently of the type of catalytically active oxidic material, to use the novel process to produce spherical and annular coated catalysts (in the coat thickness range described) whose A value is regularly from 20 to 30 m²/g. These values are unusually high for annular oxidic coated catalysts and are known in prior art processes at most for oxidic active materials having a high phosphorus content and of the hetero polyacid type (Keggin structure type).

A measure of the adhesive strength of the oxidic coat is the following turntable abrasion test, on which all adhesive strength data in this publication is based.

At room temperature, a suitable turntable (angle of inclination 45°) of polished V2A stainless steel (300 mm diameter, 100 mm edge height, no baffles) is filled to 30% of its volume with coated catalysts and rotated for 5 minutes at a speed of 35 revolutions per minute. The abraded active material produced is weighed. When the result is divided by the total amount of oxidic active material present on the coated catalysts introduced and multiplied by 100, the abrasion Ab in % is obtained.

Regardless of the type of catalytically active oxidic material, and even at the abovementioned high A values, the novel process as a rule gives spherical or annular coated catalysts whose Ab value is <10, in general 5, % by weight and, when the liquid binders stated in this publication as being particularly preferred are used, even <0.5% by weight.

It should be stated at this point that all process steps in the novel coating of the carriers with oxidic active material before the removal of the liquid binder are effected as a rule at room temperature (ie. about 25° C.).

An essential feature of the novel process is that, instead of precursor material, the catalytically active oxidic material as such is applied to the carrier. For the preparation of said material, it is usual to start in a manner known per se from suitable sources of the catalytically active, oxidic material and to produce from this material a very intimate, preferably finely divided dry mixture, which is then subjected to calcination and, if required, converted into finely divided form by milling. As is generally known, all that is important is that the sources are either already oxides or are compounds which can be converted into oxides by heating, at least in the presence of oxygen. In addition to the oxides, suitable starting compounds are therefore in particular halides, nitrates, formates, oxalates, acetates, carbonates and hydroxides.

The thorough mixing of the starting compounds can be carried out in the dry or wet form. If it is effected in dry form, the starting compounds are advantageously used as finely divided powders and, after mixing and if required compression molding, are subjected to calcination. However, thorough mixing is preferably effected in wet form. The starting compounds are usually mixed with one another in the form of an aqueous solution or suspension. The aqueous material is then dried and thereafter calcined. The drying process is preferably carried out by spray drying. The resulting powder frequently proves to be too finely divided for direct further processing. In these cases, it may be kneaded with the addition of water. The resulting kneaded material is then subjected to calcination and thereafter milled to give finely divided oxidic active material.

The calcination conditions are known per se for the various possible oxidic active materials to a person skilled in the art.

The novel process is advantageous in the case of multimetal oxide materials containin Mo and V or Mo, Fe and Bi.

The novel process proves particularly advantageous in the case of active multimetal oxides which are to be applied as a coat and are of the general stoichiometry I $$Mo_{12}V_aX_b^1X_c^2X_d^3X_e^4X_f^5X_g^6O_n \qquad (I)$$

where $X^1$ is W, Nb, Ta, Cr and/or Ce, $X^2$ is Cu, Ni, Co, Fe, Fln and/or Zn, $X^3$ is Sb and/or Bi, $X^4$ is at least one or more alkali metals, $X^5$ is at least one or more alkaline earth metals, $X^6$ is Si, Al, Ti and/or Zr, a is from 1 to 6, b is from 0.2 to 4, c is from 0.5 to 18, d is from 0 to 40, e is from 0 to 2, f is from 0 to 4, g is from 0 to 40 and n is a number which is determined by the valency and frequency of the elements differing from oxygen in I.

The preparation of the active multimetal oxides I including the calcination conditions, are described in DE-A 43 35 973. DE-A 43 35 973 also discloses preferred embodiments within the active multimetal oxides I. These include, for example, those multimetal oxides I which are covered by the following meanings of the variables of the general formula I:

$X^1$ is W, Nb and/or Cr, $X^2$ is Cu, Ni, Co and/or Fe, $X^3$ is Sb, $X^4$ is Na and/or K, $X^5$ is Ca, Sr and/or Ba, $X^6$ is Si, Al and/or Ti, a is from 2.5 to 5, b is from 0.5 to 2, c is from 0.5 to 3, d is from 0 to 2, e is from 0 to 0.2, f is from 0 to 1, g is from 0 to 15 and n is a number which is determined by the valency and frequency of the elements differing from oxygen in I.

However, very particularly preferred multimetal oxides I are those of the general formula I'

$$Mo_{12}V_aX_b^1X_c^2X_f^5X_g^6O_n \qquad (I')$$

where $X^1$ is W and/or Nb, $X^2$ is Cu and/or Ni, $X^5$ is Ca and/or Sr, $X^6$ is Si and/or Al, a is from 3 to 4.5, b is from 1 to 1.5, c as from 0.75 to 2.5, f is from 0 to 0.5, g is from 0 to 8 and n as a number which is determined by the valency and frequency of the elements differing from oxygen in I'.

Coated catalysts prepared according to the invention with the active multimetal oxides I are particularly suitable for the preparation of acrylic acid from acrolein by gas-phase catalytic oxidation. This is true in particular for spherical or annular coated catalysts, especially when they have the characteristics (geometry, coat thickness, etc.) described in this publication as being preferred. The general reaction conditions for the gas-phase catalytic oxidation of acrolein to acrylic acid are likewise described in DE-A 43 35 973.

The novel process is also suitable in the case of active multimetal oxides as used for the catalytic gas-phase oxidation of methacrolein to methacrylic acid and are described in, for example, DE-A 40 22 212.

The novel process furthermore proves suitable in the case of active multimetal oxides which are to be applied as a coat and are of the general stoichiometry II $$Mo_{12}Bi_aFe_bX_c^1X_d^2X_e^3X_f^4O_n \qquad (II)$$

where $X^1$ is nickel and/or cobalt, $X^2$ is thallium, an alkali metal and/or an alkaline earth metal, $X^3$ is phosphorus, arsenic, boron, antimony, tin, cerium, lead, niobium and/or tungsten, $X^4$ is silicon, aluminum, titanium and/or zirconium, a is from 0.5 to 5, b is from 0.01 to 3, c is from 3 to 10, d is from 0.02 to 2, e is from 0 to 5, f is from 0 to 10 and n is a number which is determined by the valency and frequency of the elements differing from oxygen in II.

The preparation of active multimetal oxides II, including the calcination conditions, are described in DE-A 40 23 239.

Coated catalysts prepared according to the invention with the active multimetal oxides II are particularly suitable for the preparation of acrolein from propene by gas-phase catalytic oxidation. This is true in particular for spherical or annular coated catalysts, especially when they have the characteristics (geometry, coat thickness, etc.) described in this publication as being preferred. The general reaction conditions for the gas-phase catalytic oxidation of propene to acrolein are likewise described in DE-A 40 23 239 and in DE-A 44 31 957.

The abovementioned coated catalysts comprising the active multimetal oxides II are, however, also suitable for the preparation of methacrolein from tert-butanol, isobutane, isobutene or tert-butyl methyl ether by gas-phase catalytic oxidation. The general reaction conditions for this catalytic gas-phase oxidation are described in, for example, DE-A 40 23 239 and DE-A 43 35 172.

The novel process is also suitable in the case of the active oxide materials of DE-A 44 05 514.

However, the novel process is of course suitable very generally for the preparation of coated catalysts based on active oxide materials, in particular for the catalytic gas-phase oxidations mentioned in this publication in connection with the evaluation of the prior art. This is also true when the oxidic active material comprises only one other element in addition to oxygen.

The advantages of the novel process are in particular the fact that the coat thickness can be varied, a high adhesive strength of the oxidic active material in combination with a completely satisfactory specific surface area thereof, greater homogeneity of the resulting coat thickness both over the surface of one carrier and over the surface of different carriers and satisfactory output of the production process.

This is true in particular of annular carriers.

EXAMPLES a) Preparation of catalytically active oxide materials

A: Catalytically active oxide material $Mo_{12}V_3W_{1.2}CU_{2.4}O_n$ 190 g of copper(II) acetate monohydrate were dissolved in 2700 g of water to give a solution I. 860 g of ammonium heptamolybdate tetrahydrate, 143 g of ammonium metavanadate and 126 g of ammonium paratungstate heptahydrate were dissolved in succession in 5500 g of water at 95° C. to give a solution II. The solution I was then stirred all at once into the solution II and the aqueous mixture was spray-dried at an outlet temperature of 110° C. The spray powder was then kneaded with 0.15 kg of water per kg of powder.

The catalyst precursor thus obtained was calcined in a through-circulation oven fed with an oxygen/nitrogen mixture. The oxygen content was adjusted so that the $O_2$ content at the outlet of the through-circulation oven was 1.5% by volume. In the calcination, the kneaded material was first heated to 300° C. at a rate of 10 K/min and then kept at this temperature for 6 hours. It was then heated to 400° C. at a rate of 10 K/min, and this temperature was maintained for a further hour. In order to realize a certain ammonia content of the calcination atmosphere, the oven loading L (g of catalyst precursor per l of internal volume of the through-circulation oven), the inlet volume flow IF (l/h (S.T.P.)) of the oxygen/nitrogen mixture and the residence time R (sec) of the oxygen/nitrogen feed (ratio of internal volume of the through-circulation oven to the volume flow of the oxygen/nitrogen mixture fed in) were chosen as follows:

L: 250 g/l;

IF: 80 l/h (S.T.P.);

R: 135 sec.

The through-circulation oven used had an internal volume of 3 l. The calcined catalytically active material was milled to a finely divided powder, 50% of the particles of said powder passing through a sieve of from 1 to 10 μm mesh size and a proportion of particles of said powder which had the longest dimension of more than 50 μm being less than 1%.

B: Catalytically active oxide material $Mo_{12}V_3W_{1.2}Cu_{1.6}Ni_{0.8}O_n$ 128 g of copper(II) acetate monohydrate and 81 g of nickel(II) acetate tetrahydrate were dissolved in 2700 g of water to give a solution I. 860 g of ammonium heptamolybdate tetrahydrate, 143 g of ammonium metavanadate and 126 g of ammonium paratungstate heptahydrate were dissolved in 5500 g of water at 95° C. to give a solution II. The solution I was then stirred all at once into the solution II and the aqueous mixture was spray-dried at an outlet temperature of 110° C. The spray powder was then headed with 0.15 kg of water per kg of powder. The kneaded material was heated in an air-fed rotary tubular oven to 400° C. in the course of 3 hours and then calcined at 400° C. for 5 hours. The calcined, catalytically active material was then milled to a finely divided powder, 50% of the particles of said powder passing through a sieve of mesh size from 1 to 10 μm and the proportion of particles of said powder which have a longest dimension of more than 50 μm being less than 1%.

b) Preparation of coated catalysts

VS1: 28 kg of annular carriers (7 mm external diameter, 3 mm length, 4 mm internal diameter, steatite, having a surface roughness $R_z$ of 45 μm and a total pore volume of ≦1% by volume, based on the volume of the carriers, producer: Hoechst Ceramtec, Germany) were introduced into a coating pan (angle of inclination 90°, Hicoater from Lödige, Germany) having an internal volume of 200 l. The coating pan was then rotated at 16 rpm. 2000 g of water was sprayed onto the carriers via a nozzle in the course of 25 minutes. 10.35 kg of the catalytically active oxide powders aA) were metered in continuously and simultaneously in the same period by means of an oscillating conveyor outside the spray cone of the atomizer nozzle. During coating, the powder fed in was completely absorbed onto the surface of the carriers, and no agglomeration of the finely divided oxidic active material was observed. After the end of the addition of powder and water, hot air at 110° C. was blown into the coating pan for 20 minutes at a speed of 2 rpm. Drying was then continued for a further 2 hours at 250° C. in a stationary bed (tray oven) under air. In the resulting annular coated catalysts, the proportion of oxidic active material was 27% by weight, based on the total weight. The coat thickness was 230±50 μm, both over the surface of one carrier and over the surface of different carriers.

S1: As for VS1, but 2000 g of an aqueous solution consisting of 75% by weight of $H_2O$ and 25% by weight of glycerol were used instead of 2000 g of water. The resulting annular coated catalysts had the same content of oxidic active material as SV1 but the range of fluctuation of the coat thickness was 230±25 μm.

S2: As for VS1, but 2000 g of an aqueous solution consisting of 75% by weight of $H_2O$ and 25% by weight of propionic acid were used instead of 2000 g of water. The resulting annular coated catalysts had the same content of oxidic active material as SV1 but the range of fluctuation of the coat thickness was 230±30 μm.

S3: As for VS1, but 2000 g of an aqueous solution consisting of 75% by weight of $H_2O$ and 25% by weight of formamide were used instead of 2000 g of water. The resulting annular coated catalysts had the same content of oxidic active material as SV1 but the range of fluctuation of the coat thickness was 230±30 μm.

S4: As for VS1, but 2000 g of an aqueous solution consisting of 75% by weight of $H_2O$ and 25% by weight of ethylene glycol were used instead of 2000 g of water. The resulting annular coated catalysts had the same content of oxidic active material as SV1 but the range of fluctuation of the coat thickness was 230±25 μm.

S5: As for VS1, but 2000 g of an aqueous solution consisting of 75% by weight of $H_2O$ and 25% by weight of 1,4-butanediol were used instead of 2000 g of water. The resulting annular coated catalysts had the same content of oxidic active material as SV1 but the range of fluctuation of the coat thickness was 230±30 μm.

S6: As for VS1, but 2000 g of an aqueous solution consisting of 75% by weight of $H_2O$ and 25% by weight of 1,6-hexanediol were used instead of 2000 g of water. The resulting annular coated catalysts had the same content of oxidic active material as SV1 but the range of fluctuation of the coat thickness was 230±25 μm.

S7: As for S1, but instead of 10.35 kg of the catalytically active oxide powder aA) the corresponding amount of the catalytically active oxide powder aB) was used. The resulting annular coated catalysts had the same content of oxidic active material as S1 but the range of fluctuation of tke coat thickness was likewise 230±25 μm.

VS2: AS for S1, but 2000 g of ethylene glycol were used instead of 2000 g of water. Separate carriers coated with active material were not obtained. Instead, multiple elements strongly adhering to one another were formed.

VS3: Example 1b) of DE-A 29 09 670 was repeated.

c) Determination of the Specific, catalytically active surface area A ($m^2$/g) and of the abrasion Ab (%) of coated catalysts from b)

Table 1 below contains the values determined for A and Ab.

TABLE 1

| Coated catalyst | A ($m^2$/g) | Ab (%) |
|---|---|---|
| VS1 | 17.5 | >10 |
| S1 | 23.2 | 0.1 |
| S2 | 17.5 | 0.3 |
| S3 | 17.4 | 0.2 |
| S4 | 23.7 | 0.1 |
| S5 | 24.3 | 0.3 |
| S6 | 28.5 | 0.2 |
| S7 | 23.0 | 0.2 |
| VS3 | 17.4 | 0.1 | d) Process for the preparation of acrylic acid from acrolein by gas-phase catalytic oxidation The coated catalysts VS1 and S1 were tested as follows in a model contact tube surrounded by a salt bath:

model contact tube: V2A stainless steel, 2 mm wall thickness, 25 mm internal diameter; 1.5 l of the model contact tube were filled with the particular coated catalyst. The reaction mixture had the following starting composition:
5% by volume of acrolein,
7% by volume of oxygen,
10% by volume of steam and
78% by volume of nitrogen.

The model contact tube was loaded with 3600 l/h (S.T.P.) of starting reaction gas mixture. The temperature of the salt bath was adjusted so that an acrolein conversion of 99 mol% resulted after a single pass.

The salt bath temperature T required for this and the selectivity S of the acrylic acid formation are shown in Table 2 below.

TABLE 2

| Coated catalyst used | T [°C.] | S [mol %] |
| --- | --- | --- |
| VS1 | 267 | 95.2 |
| S1 | 263 | 95.3 |

We claim:

1. A process for the preparation of a catalyst which consists of a carrier and a catalytically active oxide material applied to the surface of the carrier, in which the carrier is first moistened with a liquid binder, a layer of active oxide material is then bound to the surface of the moistened carrier by bringing it into contact with dry, finely divided, active oxide material, and the liquid binder is then removed from the moistened carrier coated with active oxide material, wherein the liquid binder is a solution consisting of from 20 to 90% by weight of water and from 10 to 80% by weight of an organic compound having a boiling point or sublimation temperature at atmospheric pressure of greater than 150° C.

2. A process as claimed in claim 1, wherein the liquid binder contains from 10 to 50% by weight of the organic compound.

3. A process as claimed in claim 1, wherein the liquid binder contains from 20 to 30% by weight of the organic compound.

4. A process as claimed in claim 1, wherein the organic compound is at least one compound selected from the group consisting of monohydric and polyhydric alcohols, monobasic and polybasic organic carboxylic acids, amino alcohols, monofunctional and polyfunctional organic amides, monosaccharides and oligosaccharides.

5. A process as claimed in claim 1, wherein the organic compound is at least one compound selected from the group consisting of ethylene glycol, 1,4-butanediol, 1,6-hexanediol, glycerol, glutaric acid, maleic acid, ethanolamine, diethanolamine, formamide, glucose, sucrose and lactose.

6. A process as claimed in claim 1, wherein the carrier consists of alumina, silica, clay, kaolin, steatite, pumice, aluminum silicate, magnesium silicate, silicon carbide, zirconium dioxide or thorium dioxide.

7. A process as claimed in claim 1, wherein the surface roughness $R_z$ of the carrier is from 40 to 100 μm.

8. A process as claimed in claim 1, wherein the total volume of the pores of the carrier is less than or equal to 1% by volume, based on the volume of the carrier.

9. A process as claimed in claim 1, wherein the longest dimension of the carrier is from 1 to 10 mm.

10. A process as claimed in claim 1, wherein the carrier used comprises spheres.

11. A process as claimed in claim 1, wherein the carrier used comprises hollow cylinders.

12. A process as claimed in claim 11, wherein the hollow cylinders have a length of from 2 to 10 mm, an external diameter of from 4 to 10 mm and a wall thickness of from 1 to 4 mm.

13. A process as claimed in claim 11, wherein the hollow cylinders have a length of from 3 to 6 mm, an external diameter of from 4 to 8 mm and a wall thickness of from 1 to 2 mm.

14. A process as claimed in claim 1, wherein the coat thickness of the catalytically active oxide material applied to the surface of the carrier is from 10 to 1000 μm.

15. A process as claimed in claim 1, wherein the coat thickness of the catalytically active oxide material applied to the surface of the carrier is from 100 to 500 μm.

16. A process for the preparation of a catalyst which consists of a carrier and a catalytically active oxide material applied to the surface of the carrier, wherein a process as claimed in any of one of the preceding claims is repeated periodically.

17. A process as claimed in claim 16, wherein the carrier is introduced into a rotating container which passes the carrier periodically through two successive metering apparatuses, the first of which sprays the liquid binder onto the carrier rolling in the rotating container and the second of which meters in the catalytically active oxide material in finely divided form.

18. A process as claimed in claim 1, wherein the catalytically active oxide material is a multimetal oxide containing Mo and V.

19. A process as claimed in claim 1, wherein the catalytically active oxide material is a multimetal oxide containing Mo, Fe and Bi.

* * * * *